United States Patent
Durbin et al.

(10) Patent No.: US 8,764,923 B2
(45) Date of Patent: Jul. 1, 2014

(54) LAMINATED GLAZING

(75) Inventors: Neil John Durbin, St. Helens (GB); Martin Derda, Bochum (DE)

(73) Assignees: Pilkington Automotive Deutschland GmbH, Witten (DE); Pilkington Group Limited, Merseyside (GB)

(*) Notice: Subject to any disclaimer, the term of this patent is extended or adjusted under 35 U.S.C. 154(b) by 382 days.

(21) Appl. No.: 13/121,034

(22) PCT Filed: Sep. 23, 2009

(86) PCT No.: PCT/GB2009/051241
§ 371 (c)(1), (2), (4) Date: Apr. 20, 2011

(87) PCT Pub. No.: WO2010/035031
PCT Pub. Date: Apr. 1, 2010

(65) Prior Publication Data
US 2011/0189426 A1    Aug. 4, 2011

(30) Foreign Application Priority Data
Sep. 26, 2008 (GB) .................................. 0817654.7

(51) Int. Cl.
B29C 55/02 (2006.01)
B29C 55/06 (2006.01)
B32B 3/00 (2006.01)

(52) U.S. Cl.
USPC ...... 156/102; 156/229; 264/288.4; 264/289.3

(58) Field of Classification Search
USPC ............ 156/102, 229; 264/288.4, 289.3, 291, 264/292
See application file for complete search history.

(56) References Cited

U.S. PATENT DOCUMENTS

| T861,037 I4 | 4/1969 | Christensen |
| 4,371,482 A | 2/1983 | Farabaugh |

(Continued)

FOREIGN PATENT DOCUMENTS

| CA | 2076420 | 7/1999 |
| DE | 1 961 148 A1 | 6/1971 |

(Continued)

OTHER PUBLICATIONS

Search Report dated Feb. 25, 2009, issued by the British Patent Office in corresponding British Patent Application No. 0817654.7.

(Continued)

*Primary Examiner* — Michael Tolin
(74) *Attorney, Agent, or Firm* — Buchanan Ingersoll Rooney PC

(57) ABSTRACT

A laminated vehicle glazing comprising a first ply of a glazing material and a second ply of a glazing material having a substantially co-extensive ply of an interlayer material laminated there between, at least a portion of the ply of interlayer material having a wedged cross-section, wherein the ply of interlayer material is pre-shaped by stretching such that either: (a) when the wedge angle is calculated at a plurality of points across the glazing, by taking measurements of a deflection of a laser beam as it passes through the glazing, the standard deviation in the magnitude of the wedge angle of the wedged portion is less than 0.05 mrad; or (b) when a grid pattern is projected onto the glazing, the standard deviation in the displacement between observed primary and secondary images of portions of the grid is less than 0.85 mm.

6 Claims, 7 Drawing Sheets

(56) References Cited

U.S. PATENT DOCUMENTS

| | | | |
|---|---|---|---|
| 5,013,134 A * | 5/1991 | Smith | 359/630 |
| 5,087,502 A * | 2/1992 | Esposito et al. | 428/156 |
| 5,130,174 A | 7/1992 | Esposito | |
| 5,137,673 A | 8/1992 | Bourcier et al. | |
| 5,648,034 A * | 7/1997 | van de Velde Keyser | 264/160 |
| 5,762,979 A | 6/1998 | Van De Velde Keyser | |
| 5,812,332 A | 9/1998 | Freeman | |
| 6,500,305 B1 * | 12/2002 | Winheim et al. | 162/207 |
| 2001/0044010 A1 | 11/2001 | Freeman | |
| 2002/0008926 A1 | 1/2002 | Freeman | |
| 2002/0172804 A1 | 11/2002 | Sauer | |
| 2004/0053006 A1 | 3/2004 | Omizu et al. | |
| 2004/0109251 A1 | 6/2004 | Freeman | |
| 2004/0166288 A1 | 8/2004 | Travis et al. | |
| 2005/0142332 A1 | 6/2005 | Sauer | |
| 2005/0158520 A1 | 7/2005 | Freeman | |
| 2006/0210776 A1 | 9/2006 | Lu et al. | |
| 2007/0009714 A1 | 1/2007 | Lee et al. | |

FOREIGN PATENT DOCUMENTS

| | | |
|---|---|---|
| EP | 0 317 545 A2 | 5/1989 |
| EP | 0 420 228 A2 | 4/1991 |
| EP | 1 800 855 A1 | 6/2007 |
| EP | 2 017 237 A1 | 1/2009 |
| GB | 1 145 353 A | 3/1969 |
| WO | WO 91/06031 A1 | 5/1991 |
| WO | WO 94/00787 A1 | 1/1994 |
| WO | WO 02/103434 A1 | 12/2002 |
| WO | WO 2006/122305 A2 | 11/2006 |
| WO | WO 2009/071135 A1 | 6/2009 |

OTHER PUBLICATIONS

International Search Report (PCT/ISA/210) issued on Jan. 19, 2010, by British Patent Office as the International Searching Authority for International Application No. PCT/GB2009/051241.

* cited by examiner

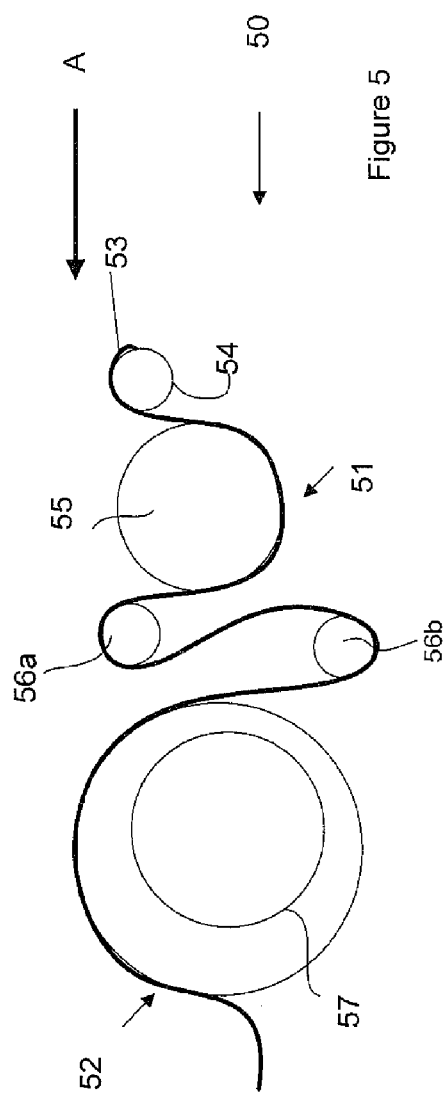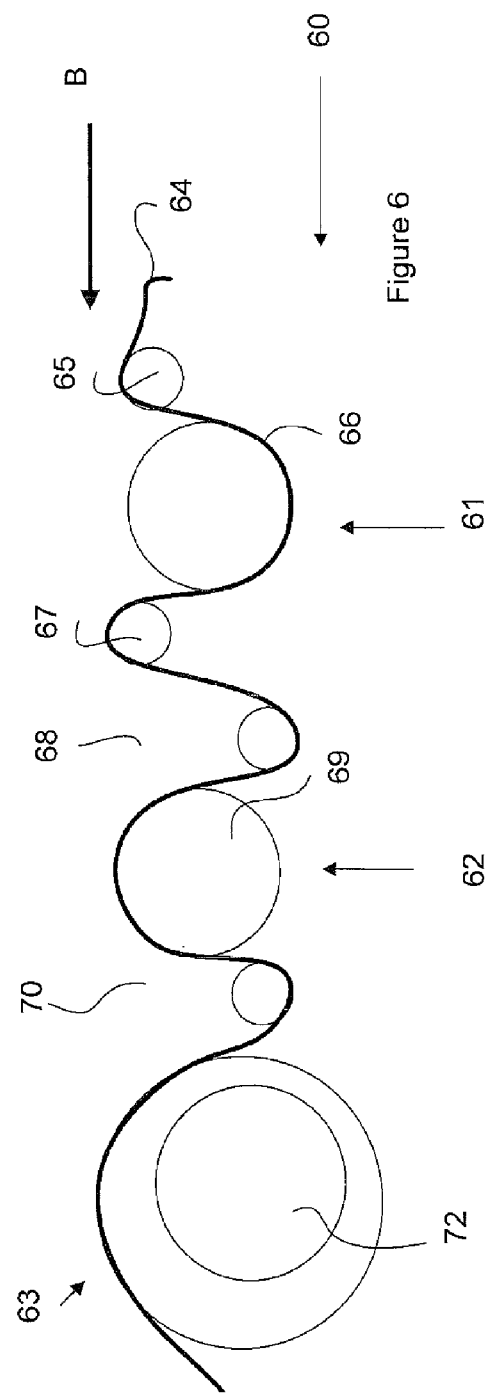

LAMINATED GLAZING

The present invention relates to a laminated glazing, in particular a laminated glazing having a curvature and being bonded together using a ply of a stretched interlayer material. The invention also relates to a method of pre-shaping a ply of interlayer material.

The use of laminated glazings in vehicles is widespread, with all windscreens conforming to European, US and Japanese safety regulations being laminated, as well as an increasing number of backlights, sidelights and rooflights. One particular issue for windscreens and is where a double or secondary image is seen when viewing an object through the glass. The effect is caused by thickness variations within the glass, present in varying degrees, and due to the shape of the screen and possible shaping errors introduced during manufacture. FIG. 1 is a schematic illustration of how a secondary image arises within a wedge. An observer 10 views a distant object 11 through a windscreen 12. The windscreen 12 varies in thickness in the region through which the observer 10 is looking. The screen effectively acts as a localised wedge refracting light as it passes through the glass. At the inner glass/air interface some light is reflected towards the outer glass/air interface, from which in due course some light is reflected back towards the driver, who thus observes a much weaker secondary image displaced by an angle θ from the primary image. The angle θ indicates the divergence of the secondary image from the primary image of the object and is dependent of the amount of wedge or curvature in the glass at the point of viewing.

Excessive levels of secondary image are disconcerting for the driver of a vehicle in which the windscreen is fitted and also give rise to safety concerns. Under ECE R43, the amount of secondary image allowable within a windscreen is measured in terms of the divergence angle θ between the primary and the secondary image. The maximum acceptable divergence angle at present is 15 arc minutes.

Aside from issues arising from secondary images in the peripheral regions of a windscreen, a second problem arises with secondary images seen within a head-up display region, which is positioned in the central, visible region of a windscreen. Although the instruments present on the dashboard of a vehicle provide vital information to a driver, when looking at the instruments, the driver is distracted from the road. Research has shown that the repetitive change in focus between the instrument panel and the road ahead is a major factor in increased driver fatigue on long journeys. One approach to eliminating the need to repeatedly look at the instrument panel is to employ a head-up display, or HUD. Head-up displays were originally developed for military use, such as in fighter aircraft, to minimise distraction, and comprised a means of displaying information in a pilot's or driver's field of view. HUDs were first included in automotive vehicles in the late 1980s, and offered a way of displaying information on the glazing of a vehicle, allowing the driver to focus easily on the road ahead whilst viewing information usually shown on the instrument panel or dashboard.

In a vehicle, a HUD works by reflecting an image off the glazing into the driver's field of view. The image is generated below the glazing, by a unit positioned on or in the dashboard, and projected upwards towards the glazing. The unit typically comprises at least one light source, such as an LED (light-emitting diode), illuminating a thin film transistor display, for example, an LCD (liquid crystal display). If coloured light sources are used, the HUD may display coloured information or indicia onto the glazing. To create the display, an image is generated on the LCD, illuminated from behind and projected onto the glazing. The projection may be direct onto the glazing, or via mirrors and/or polarizers to produce a sharp and clear image.

If a sufficiently large wedge angle is present in the HUD region, or even if the wedge angle, although small, varies across the viewing area, the image generation can not only be uncomfortable for the vehicle driver, but also dangerous, as it may be difficult to see of distinguish the images projected.

One solution to this problem is to use a ply of interlayer material within the laminated glazing with a specific wedged cross-section across at least a portion of the interlayer material. This can be either: across the entire glazing (fully wedged cross-section), and as illustrated schematically in FIG. 2 or only in the region where the HUD will be viewed (partially wedged cross-section), as illustrated schematically in FIG. 3. FIG. 4 is a schematic illustration of the specific HUD region within a laminated glazing where the interlayer material has a fully wedged cross-section. The laminated glazing 40 comprises first 41 and second 42 panes of a glazing material, such as annealed silicate float glass, having a complex curvature (one having a curvature in both x- and y-directions). These panes are bonded together by a ply 43 of fully wedged interlayer material. In the enlarged region, the wedge angle is shown to vary owing to the processing required to laminate the two complex curved panes together. This variation could lead to difficulties in seeing the images projected as part of the HUD. (The overall effect is exaggerated for the purposes of illustration.)

The use of fully and partially wedged interlayer materials is widely known, and disclosed, for example, in U.S. Pat. No. 5,812,332, U.S. T 861,037, DE1961148 and EP 1 880 243 A1. However, whilst the use of fully or partially wedged interlayer materials is commonplace, once the interlayer material has been processed in forming a laminated glazing, which, in the case of a windscreen, has curvature in at least one of x- or y-directions, it is difficult to control the variation of the wedge angle within the HUD region. Consequently, the second of the two problems outlined above still exists.

It is therefore desirable to be able to produce a laminated glazing employing a fully or partially wedged interlayer material in which the variation of the wedge angle in specific regions of the laminated glazing can be controlled.

The present invention aims to address these problems by providing a laminated vehicle glazing comprising a first ply of a glazing material and a second ply of a glazing material having a substantially co-extensive ply of an interlayer material laminated therebetween, at least a portion of the ply of interlayer material having a wedged cross-section, wherein the ply of interlayer material is pre-shaped by stretching such that either:

(a) when the wedge angle is calculated at a plurality of points across the glazing, by taking measurements of a deflection of a laser beam as it passes through the glazing, the standard deviation in the magnitude of the wedge angle of the wedged portion is less than 0.05 mrad; or (b) when a grid pattern is projected onto the glazing, the standard deviation in the displacement between observed primary and secondary images of portions of the grid is less than 0.85 mm.

By providing an interlayer material with a wedged region in which the standard deviation of the wedge angle is minimised, a glazing having superior optical quality in this wedged region can be obtained.

Taking measurements of a deflection of a laser beam as it passes through the glazing may involve the use of an expander, a focal length lens and a high precision position detector to measure the wedge angle inside the glazing.

Theory in this field shows that a laser beam passing through a wedged ply will produce a deflection. The total deflection in a glazing is the result of the wedge and glass optics. If the glass is curved, the glass will have greater optical power and this also will lead to a beam deflection, regardless of whether the ply of interlayer material has a wedged cross-section. Therefore it is advantageous for the laser to be perpendicular to glass surfaces to avoid any wrong measurement and to enable the attainment of the desired wedge angle.

The ply of interlayer material may have a partially wedged or a fully wedged cross-section.

The standard deviation in the magnitude of the wedge angle may be less than 0.045 mrad, preferably less than 0.04 mrad, more preferably less than 0.035 mrad.

The standard deviation in the displacement between observed primary and secondary images of portions of the grid may be less than 0.70 mm, preferably less than 0.50 mm, more preferably less than 0.35 mm, even more preferably less than 0.20 mm, and most preferably less than 0.15 mm.

The ply of interlayer material may be a ply of polyvinyl butyral interlayer material (PVB).

The present invention also provides a method of pre-shaping a ply of interlayer material for use in a laminated glazing, wherein at least a portion of the ply of interlayer material has a wedged cross-section, by stretching at least a portion of the ply of interlayer material, the method comprising:
in a first step, providing heat and moisture to a first surface of the ply of interlayer material to perform a first heating stage;
in a second step, providing heat and moisture to a second surface of the ply of interlayer material, opposite the first surface, to perform a second heating stage; and
in a third step, stretching the ply of interlayer material into a desired shape;
wherein in the first and second steps, the rate at which the heat and moisture are supplied is controlled such that the shaping of the ply of interlayer material is uniform, and the standard deviation in the magnitude of the wedge angle of the wedged portion of the interlayer material is less than 0.05 mrad.

The standard deviation in the magnitude of the wedge angle of the wedged portion may be less than 0.045 mrad, preferably less than 0.04 mrad, more preferably less than 0.035 mrad.

Preferably, the first step is carried out by passing the ply of interlayer material over the surface of a first rotating drum, and the heat and moisture is provided by water. This arrangement is advantageous because it enables better control of the temperature of the drum.

Preferably, the second step is carried out by passing the ply of interlayer material over the surface of a second rotating drum, and the heat and moisture is provided by water. As above, this arrangement is advantageous because it enables better control of the temperature of the drum.

The method may further comprise the step of laminating the ply of pre-shaped interlayer material between two plies of a glazing material.

The present invention also provides a laminated glazing comprising the pre-shaped ply of interlayer material formed using the method discussed above.

It will be appreciated that optional features applicable to one aspect of the invention can be used in any combination, and in any number. Moreover, they can also be used with any of the other aspects of the invention in any combination and in any number. This includes, but is not limited to, the dependent claims from any claim being used as dependent claims for any other claim in the claims of this application.

The invention will now be described by way of example only, and with reference to the accompanying drawings, in which:

FIG. 5 is a schematic diagram of an interlayer material shaping apparatus;

FIG. 6 is a schematic diagram of the wedge shaping apparatus used in the performance of the invention;

Figure 1:
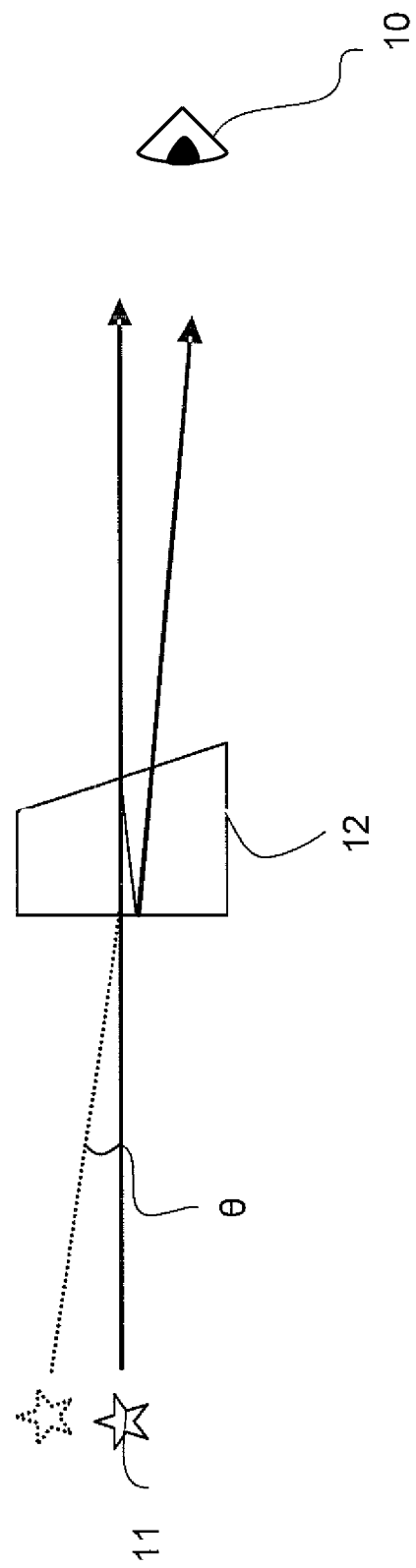
FIG. 1 (referred to above) is schematic illustration of how a secondary image arises within a wedge.
Figure 2:
FIG. 2 (referred to above) is a schematic illustration of a fully wedged interlayer material.
Figure 3:
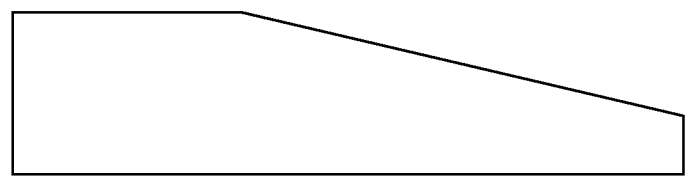
FIG. 3 (referred to above) is a schematic illustration of a partially wedged interlayer material.
Figure 4:
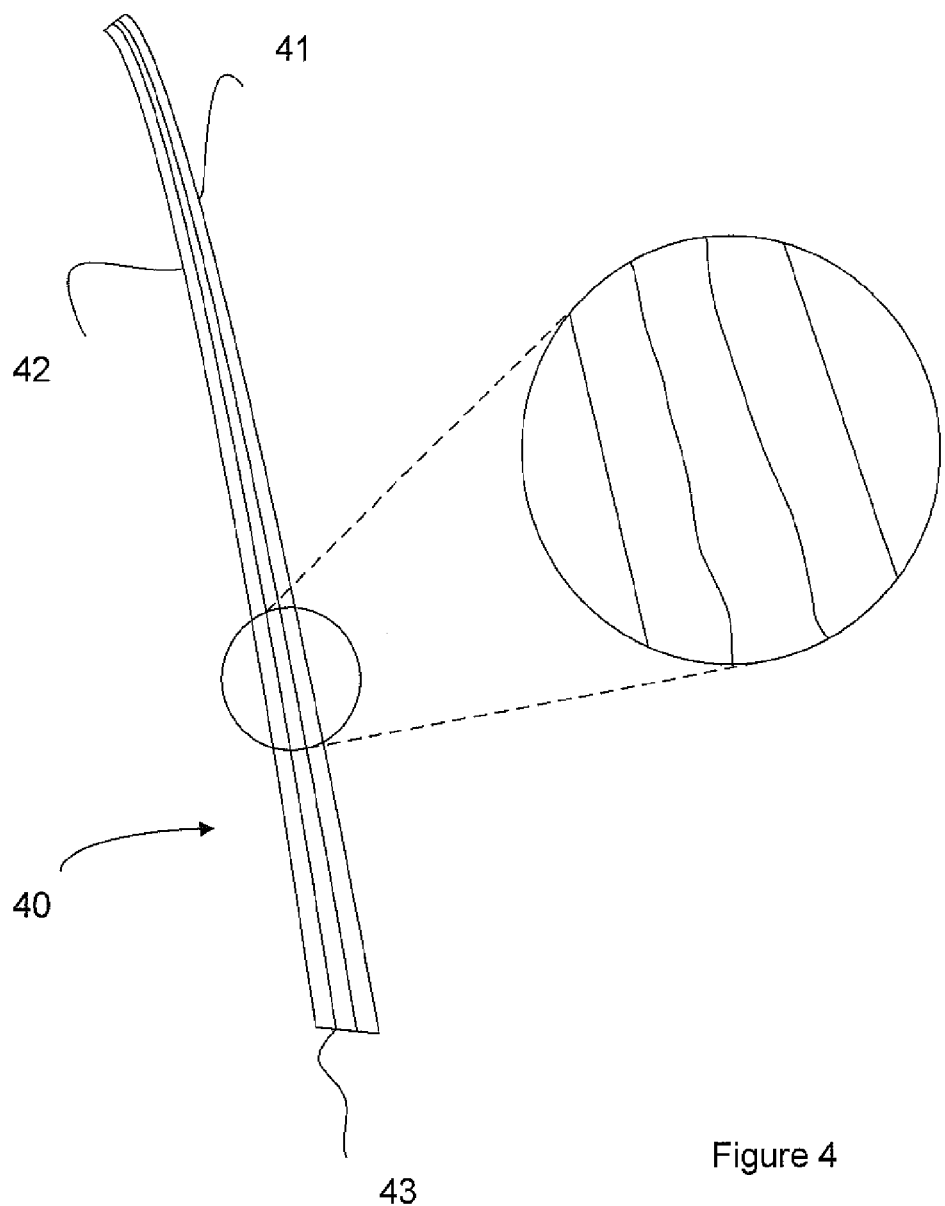
FIG. 4 (referred to above) is a schematic illustration of the specific HUD region within a laminated glazing where the interlayer material has a fully wedged cross-section.

In the present invention, it has been found surprisingly that the standard deviation in the wedge angle at any point within a partially or fully wedged interlayer material can be controlled to a high degree by using an interlayer material shaping system originally intended for shaping standard, non-wedged interlayer materials. By pre-shaping the interlayer material by stretching, the wedge in a final, laminated glazing can be finely controlled, leading to a windscreen having a higher optical quality, either overall, or in a specific area, such as a HUD region. Depending on the stretching parameters heat, speed and radius of the expanding cone, an increase in the wedge angle of a ply of interlayer material, as a result of the pre-shaping of this invention, within 0.1-0.18 mrad is achievable. Such a small range is beneficial because it enables fine tuning to the desired wedge angle. In the following discussion, the interlayer materials used are polyvinyl butyral interlayer materials, as these are the most commonly used within laminated windscreens and other vehicle glazings. However, the present invention is equally applicable to other interlayer material types.

Generally, PVB interlayer materials are shaped by a stretching process under specific temperature and humidity conditions. This is done to shape the PVB material into a substantially arcuate shape so as to be a better match to the shape of the final windscreen, and to ensure that the maximum number of windscreen-shaped blanks possible can be cut from a single roll of commercially available interlayer material. A typical shaping apparatus for constant thickness of PVB interlayer material of from 0.36-0.78 mm is illustrated schematically in FIG. 5 (with the PVB interlayer material flow direction marked by arrow A). The shaping apparatus 50 comprises a heating drum arrangement 51 and an expanding cone arrangement 52. PVB interlayer material 53 is fed from an unwinding station (not shown) and enters the apparatus 50 by passing over a first roller 54 and onto a rotating drum 55. The PVB interlayer material 53 is heated as it passes over the surface of the rotating drum 55. This allows the PVB material 53 to stretch and obtain the desired shape. The drum 55 is formed from a steel sheet, and has an outer PTFE (polytetrafluoroethylene) coating. The PVB material 53 then passes over a second roller 56a and a lay-on roller 56b before contacting an expanding cone 57. At the point the interlayer material 53 leaves the second roller 46 it has been heated to a temperature above its glass transition point $T_g$. This allows plastic deformation to take place. The expanding cone 57 comprises a series of slats joined together to form a conic frustum. Similar to an umbrella opening, the slats move apart gradually as the PVB interlayer material 53 passes over the expanding cone 57. However, unlike and umbrella, the narrow end of the conic frustum expands, increasing its diameter, with a maximum increase resulting in both ends of the conic frustum having the same radius. The amount of expansion is determined by the type of interlayer material 53 used, the desired stretch and the processing conditions. One side of the expanding cone 57 is cooled to maintain the shape of the stretched PVB interlayer material 53, which is now in the form of a continuous arc. The PVB material 53 then passes out of the shaping apparatus 50 to a cutting machine for cutting windscreen blanks from the now arcuate PVB material 53 (not shown).

In the present invention, a second rotating drum is employed to give greater control when shaping fully or partially wedged PVB material with a thickness from 0.74-1.4 mm. FIG. 6 is a schematic illustration of the shaping apparatus used in the present invention (with the PVB interlayer material flow direction marked by arrow B). The shaping apparatus 60 comprises a first heating drum arrangement 61, a second heating drum arrangement 62 and an expanding cone arrangement 63. PVB interlayer material 64 is fed from an unwinding station (not shown) and enters the apparatus 60 by passing over a first roller 65 and onto a rotating drum 66. The PVB interlayer material 64 is heated as it passes over the surface of the rotating drum 66. This allows the PVB material 64 to stretch and obtain the desired shape. The drum 66 is formed from a steel sheet, and has an outer PTFE (polytetrafluoroethylene) coating. Only one surface of the PVB material 64 touches the rotating drum 66. The PVB material 64 then passes over a second roller 67 out of the first heating drum arrangement 61 and onto a third roller 68 into the second heating drum arrangement 62. The PVB interlayer material 64 is heated as it passes over the surface of the rotating drum 69. This allows the PVB material 64 to stretch and obtain the desired shape. The second heating drum arrangement 62 is positioned such that the opposite surface of the PVB material 64 that did not contact the first rotating drum 66 is now in contact with the second rotating drum 69. The PVB material 64 then exits the second heating drum arrangement 62 via a fourth roller 70 and onto an expanding cone 71. At the point the interlayer material 64 leaves the fourth roller 70 it has been heated to a temperature above its glass transition point $T_g$. This allows plastic deformation to take place. The expanding cone 71 comprises a series of slats joined together to form a conic frustum. Similar to an umbrella opening, the slats move apart gradually as the PVB interlayer material 64 passes over the expanding cone 71. However, unlike and umbrella, the narrow end of the conic frustum expands, increasing its diameter, with a maximum increase resulting in both ends of the conic frustum having the same radius. The amount of expansion is determined by the type of interlayer material 64 used, the desired stretch and the processing conditions. Ideally, the stretching process takes place in a humidity controlled room, such that the amount of moisture present in the final, stretched PVB interlayer material is the same or as close as possible to the amount of moisture in the original PVB interlayer material. One side of the expanding cone 71 is cooled to maintain the shape of the stretched PVB interlayer material 64, which then passes out of the shaping apparatus 60 to a cutting machine for cutting windscreen blanks from the now arcuate PVB material 64 (not shown).

By using a second heating drum arrangement, it is possible to finely control the variation of the wedge angle in various regions of the partially or fully wedged PVB material at the same time as providing an arcuate roll of material from which windscreen blanks can be cut.

In order to test whether this double-heating firstly enabled a continuous arc of partially or fully wedged PVB material to be produced, trials were carried out using two commercially available PVB materials, one being fully wedged, and one being partially wedged.

The fully wedged product chosen was Solutia RW41 PVB, which has a wedge across the roll of the interlayer material having a minimum thickness of 0.76 mm at the thinnest edge of the wedge. Processing conditions for this fully wedged product are given in Table 1 below. The partially wedged product chosen was Butacite™ Wedge available from DuPont, again having a minimum thickness at the thinnest edge of 0.76 mm. Tables 1 and 2 show the roll width and shape height achieved after processing for both fully (Table 1) and partially (Table 2) wedged products:

TABLE 1

Material details for shaping trial of fully wedged PVB product

| Test No. | Roll Width | | Shape height (radius) (mm) |
|---|---|---|---|
| | Initial (m) | After shaping (m) | |
| 1 | 0.985 | 0.902 | 32.0 |
| 2 | 0.985 | 0.922 | 34.0 |
| 3 | 0.995 | 0.940 | 38.5 |
| 4 | 0.995 | 0.922 | 39.0 |

TABLE 2

Material details for shaping trial of partially wedged PVB product

| Test No. | Roll Width | | Shape height (radius) (mm) |
|---|---|---|---|
| | Initial (m) | After shaping (m) | |
| 1 | 0.955 | 0.873 | 44 |
| 2 | 0.955 | 0.866 | 33 |
| 3 | 0.955 | 0.867 | 34 |

In order to shape the material, the line speed at the first rotating drum was kept within the range 3 to 8 m/min, and the lined speed at the second rotating drum in the range 3 to 8 m/min. The line speed at each drum, and the heating of each drum was altered to ensure that the temperature of the PVB interlayer material was above $T_g$ at the point it exited the fourth roller onto the expanding cone. The tests were carried out in a humidity controlled room, ensuring that the moisture content of the PVB interlayer material was kept as constant as possible before, during and after processing.

Following these trials, it was determined that use of two rotating drums gave good contact between both surfaces of the PVB and the steam, leading to even temperature control and little lensing effect (where objects viewed through the interlayer material appear distorted) within the shaped PVB.

Once shaped, the interlayer material may subsequently be laminated between at least two plies of a glazing material, to form a laminated glazing.

Once it had been concluded that both fully and partially wedged PVB products could be shaped successfully, it was decided to produce laminated samples containing pre-shaped and unshaped fully and partially wedged PVB to examine the effect of shaping on the standard deviation of the wedge angle within a HUD region in a windscreen. More than 5 samples were laminated using a variety of interlayer materials (standard i.e. non-wedged, fully wedged and partially wedged) using the same standard process. Initially, a shaped interlayer material blank corresponding approximately to the shape of the curved glass plies used to form the glazing was laid up on a first ply of glass. The second ply of glass was then placed on top of the interlayer material, and aligned with the first ply of glass, forming a laminate assembly. Excess interlayer material was then trimmed from around the edge of the laminate assembly, which was passed through a nip roller for initial de-airing. Once de-aired, the laminate assembly was placed in an autoclave at 140° C. and a pressure of 10 to 15 bar, until fully bonded. Each ply of glass used had a thickness of 1.8 mm, tinted light green in colour with a light transmission (CIE Illuminant A) of 80%.

In order to determine the standard deviation of the wedge angle across the HUD region of the glazing, a laser beam method was used. This is where a series of laser point light sources is viewed through the glazing at various positions, and the deflection of laser of each point light source recorded.

Measurements were taken starting at a distance of 0.05 m from the edge of the obscuration band, 0.2 m from the left hand edge of the windscreen. Data was collected along a line, with laser beams distanced every 0.01 m. Table 3 summarises the glazing constructions and the value of the wedge angle calculated in mrad for all samples. All measurement points are nominal positions.

TABLE 3

Summary of wedge angle data

| PVB Type | Shaped | Specified wedge angle [mrad] | Measured wedge angle [mrad] | Standard deviation wedge angle [mrad] |
|---|---|---|---|---|
| Partially wedged | No | 0.33 | 0.313 | 0.055 |
| Partially wedged | Yes | 0.36 | 0.369 | 0.015 |
| Fully wedged | No | 0.5 | 0.494 | 0.071 |
| Fully wedged | Yes | 0.5 | 0.48 | 0.032 |

The position of the observed secondary image changes with respect to the primary image dependent upon the wedge angle. For an un-wedged, standard interlayer material, the secondary image appears above the primary image (undercompensation). As the wedge angle increases, the secondary image moves towards the primary image. If the wedge angle is too great, the secondary image appears below the primary image (overcompensation). In table 4 below, the magnitude of the observed secondary image by using a sample grid is quoted, with no reference to whether the secondary image is under or overcompensated.

The standard deviation, σ, in the ghosting distance measurement was also calculated, as summarised in Table 4, using the following formula:

TABLE 4

Standard deviation in the ghosting distance measurement for different runs, each with a minimum of 5 samples $$\sigma = \sqrt{\frac{n\Sigma x^2 - (\Sigma x)^2}{n(n-1)}}$$

| Sample | PVB type | Shaped | σ (mm) |
|---|---|---|---|
| 'Run 1 | Fully wedged | Yes | 0.0582 |
| Run 2 | Fully wedged | Yes | 0.100 |
| Run 1 | Fully wedged | No | 0.869 |
| Run 2 | Fully wedged | No | 0.962 |

By using the shaping process, it is possible to control the standard deviation in the ghosting distance measurement across the HUD region of a windscreen for both fully and partially wedged PVB interlayer materials. For fully wedged products, the maximum standard derivation in ghosting distance measurements was 0.100 mm for shaped material, compared with 0.962 mm for unshaped material.

The improvement in the quality of the optical measurements found during these trials was unexpected and surprising. Shaping standard (non-wedged) PVB interlayer material normally results in inferior optical quality of the resulting laminated glazing when viewed in transmission. When standard PVB interlayer material is shaped, the shaping process produces a wedge within the material. However, the wedge produced is not uniformly shaped, and varies across the width of the blank, and consequently the glazing. This inhomogeneity causes the observed optical distortion.

The positive influence of the shaping process on optical quality is also observed by measuring the spacing between primary and secondary images (or "ghosting" of images) projected onto the actual HUD area of a windscreen. The use of a wedged interlayer material with the thick end of the wedge at the top of the windscreen causes the spacing between the two images to be reduced. The use of a shaped wedged interlayer material should therefore give improved optical quality and reduced ghosting of images when compared to un-shaped wedged interlayer material.

Figure 7:
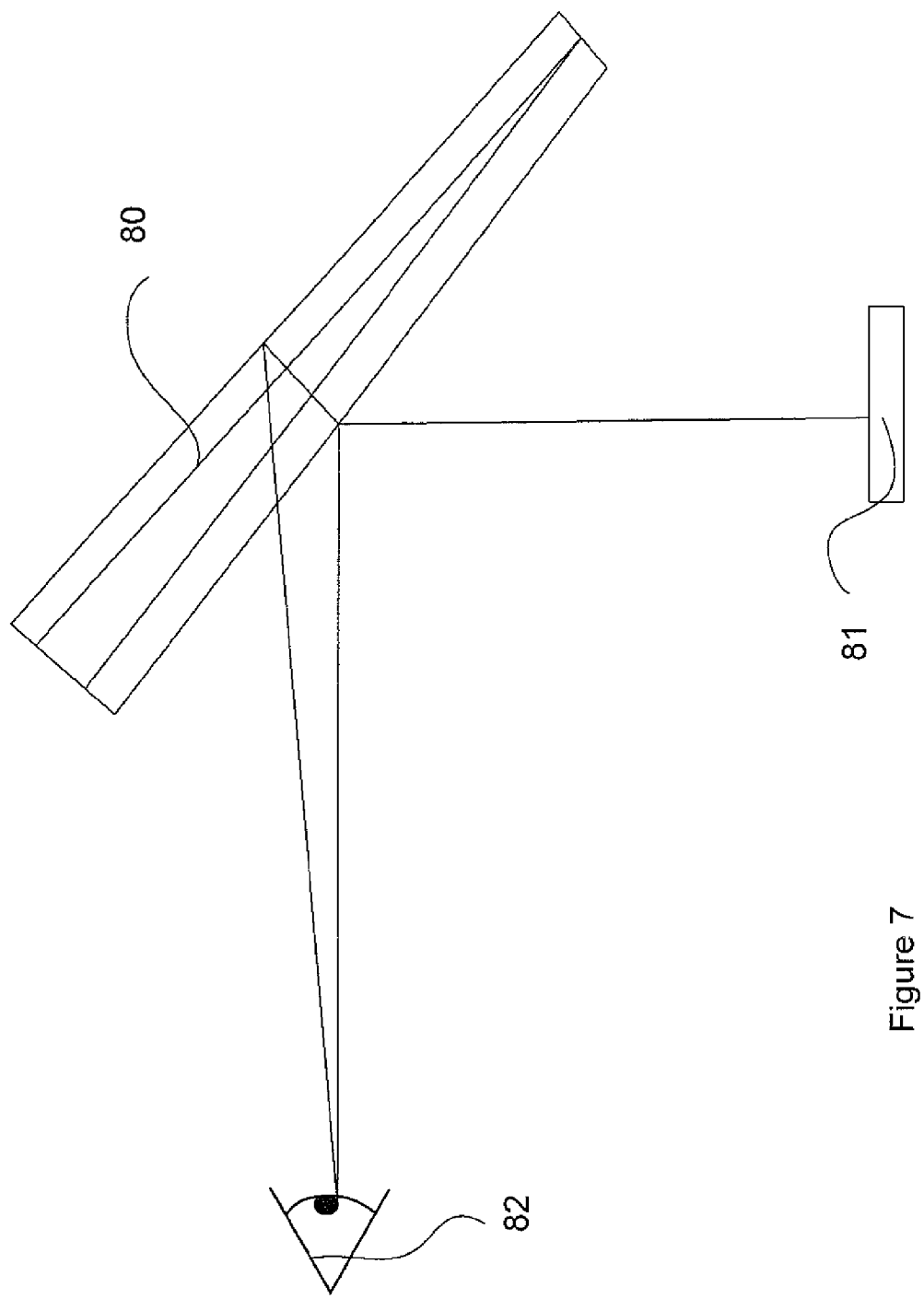
FIG. 7 is a schematic cross-section showing an experimental measurement set up for measuring ghosting of images projected onto a HUD region.

FIG. 7 is a schematic cross-section showing an experimental measurement set up for measuring ghosting of images projected onto a HUD region. The laminated glazing 80 is positioned on a stand (not shown) at the same rake angle as when installed within a vehicle. A HUD projector 81 is positioned beneath the laminated glazing 80 so as to project images onto the HUD area as if it were installed in a vehicle. A camera 82 is positioned in the centre of the "eyebox" area, so-called because this is the region in which the eye of a driver is most likely to be when driving. The camera 82 is provided with a lens having a focal distance of 35 mm or 50 mm, depending on the laminated glazing 80 being analysed. Typically, the camera will be placed at a distance of between 600 and 1000 mm from the inner surface of the laminated glazing 80 (the actual distance is again dependent on the laminated glazing being analysed), at an angle of between 5 and 8° to the horizontal, mimicking the slight downward look of a vehicle driver.

Figure 8A:
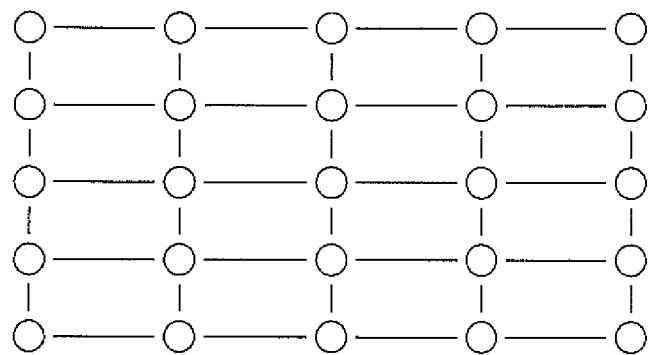
FIG. 8a shows a first grid pattern.
Figure 8B:
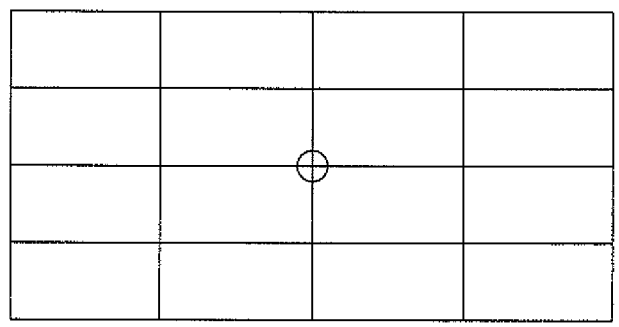
FIG. 8b shows a second grid pattern.
Figure 8C:
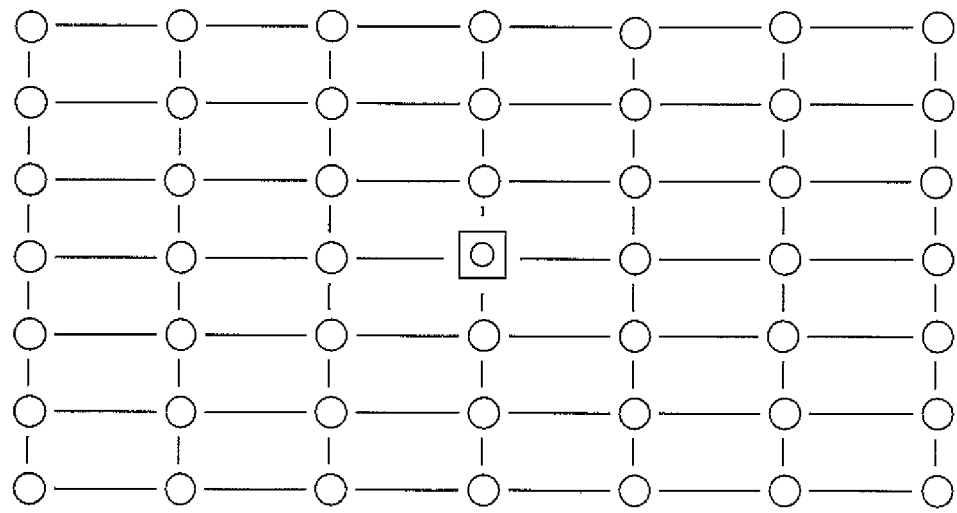
FIG. 8c shows a third grid pattern.

FIGS. 8a, 8b and 8c show first, second and third grid patterns projected onto the HUD region of the laminated glazing 80 (not to scale) during testing. FIG. 8a shows a grid pattern having an open circle at each grid line intersection. The width of the grid pattern is 169.74 mm, and the height 76.3 mm, with a horizontal line length between the open circles of approximately 20 mm, and a line thickness in the range 0.5 to 0.8 mm.

FIG. 8*b* shows a grid pattern having a single open circle at the central grid line intersection. The grid pattern itself is essentially the same as that shown in FIG. 8*a*.

FIG. 8*c* shows a grid pattern approximately landscape orientation A4 (297 mm×210 mm) in size, with a horizontal line length (between grid intersections) in the range 25 to 29 mm, and a line thickness in the range 0.5 to 0.8 mm. An open circle is positioned at each grid intersection, with an open square also being positioned at the central grid intersection.

Figure 9A:
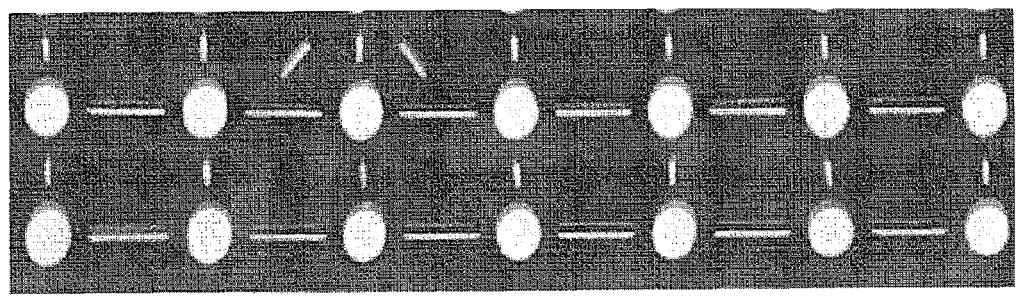
FIG. 9a is a photograph showing the positions of the primary and secondary images of the third grid pattern (FIG. 8c) for a laminated glazing comprising a non-wedged interlayer material.
Figure 9B:
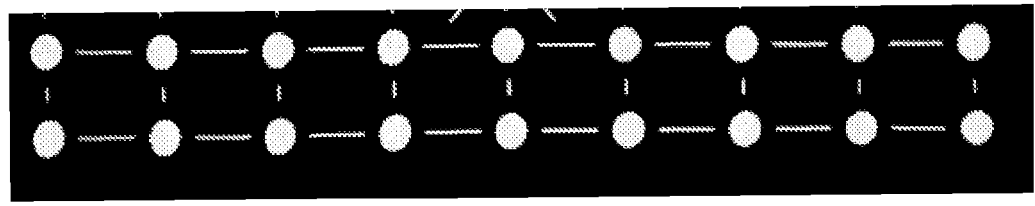
FIG. 9b is a photograph showing the positions of the primary and secondary images of the third grid pattern (FIG. 8c) for a laminated glazing comprising a wedged interlayer material.

To illustrate the observations made, FIG. 9*a* is a photograph showing the positions of the primary and secondary images of the third grid pattern (FIG. 8*c*) for a laminated glazing comprising a non-wedged interlayer material. The secondary image is visible above the position of the primary image. FIG. 9*b* is a photograph showing the positions of the primary and secondary images for the same grid, this time for a laminated glazing comprising a wedged interlayer material. The secondary image is visible below the position of the primary image, but the separation between the images is much reduced.

The calculation of the position of the images and their relative displacement, and therefore the amount of ghosting, is carried out by analysing each horizontal line within the viewed projected grid.

Therefore the observed optical quality of a HUD projected onto a laminated glazing is improved by using a shaped fully wedged PVB interlayer material. Preferably, the standard deviation in the displacements between observed primary and secondary images of a grid projected onto a laminated glazing comprising a shaped wedged (fully or partially) interlayer material is less than 0.5 mm.

Although the shaping method described above has been applied to HUD regions in vehicle windscreens, it is equally applicable to other vehicle glazing applications where it is desirable to be able to produce a specified wedge angle and/or minimised standard deviation in wedge angle. For example, the shaping method may be used to produce improved wedge interlayer materials for use in large area glazings, such as cielo windscreens.

In the above examples, each laminated sample was made from two plies of light-green tinted silicate float glass. However, any suitable glazing material may be used instead. Such glazing materials include clear or tinted silicate float glass (which may be annealed, fully toughened, semi-toughened and/or coated), and plastics materials, such as polycarbonate.

The invention claimed is:

1. A method of pre-shaping a ply of interlayer material for use in a laminated glazing, wherein at least a portion of the ply of interlayer material has a wedged cross-section before the pre-shaping, by stretching at least a portion of the ply of interlayer material, the method comprising:
   in a first step, providing heat and moisture to a first surface of the ply of interlayer material to perform a first heating stage;
   in a second step, providing heat and moisture to a second surface of the ply of interlayer material, opposite the first surface, to perform a second heating stage; and
   in a third step, stretching the ply of interlayer material into a desired shape;
wherein in the first and second steps, the rate at which the heat and moisture are supplied is controlled such that the shaping of the ply of interlayer material is uniform, and the standard deviation in the magnitude of the wedge angle of the wedged portion of the interlayer material after the pre-shaping is less than 0.05 mrad,
   wherein the first step is carried out by passing the ply of interlayer material over the surface of a first rotating drum, and the heat and moisture is provided by water, and
   wherein the second step is carried out by passing the ply of interlayer material over the surface of a second rotating drum, and the heat and moisture is provided by water.

2. The method of claim 1, further comprising the step of laminating the pre-shaped ply of interlayer material between two plies of a glazing material.

3. The method of pre-shaping of claim 1, wherein the standard deviation in the magnitude of the wedge angle of the wedged portion is less than 0.045 mrad.

4. The method of pre-shaping of claim 1, wherein the standard deviation in the magnitude of the wedge angle of the wedged portion is less than 0.04 mrad.

5. The method of pre-shaping of claim 1, wherein the standard deviation in the magnitude of the wedge angle of the wedged portion is less than 0.035 mrad.

6. The method of pre-shaping of claim 1, wherein the method imparts an arcuate shape to the ply of interlayer material.

* * * * *